United States Patent [19]
Kissinger

[11] Patent Number: 6,130,359
[45] Date of Patent: Oct. 10, 2000

[54] LIQUID VACUUM PUMP SEAL TO REDUCE CONTAMINATION IN BISPHENOL-A

[75] Inventor: Gaylord M. Kissinger, Evansville, Ind.

[73] Assignee: General Electric Company, Schenectady, N.Y.

[21] Appl. No.: 09/154,289

[22] Filed: Sep. 16, 1998

[51] Int. Cl.[7] ..................................................... C07L 39/16
[52] U.S. Cl. ........................................... 568/728; 568/724
[58] Field of Search ..................................... 568/728, 724

[56] References Cited

U.S. PATENT DOCUMENTS

| | | |
|---|---|---|
| 4,461,915 | 7/1984 | Mendiratta et al. . |
| 4,876,391 | 10/1989 | Kissinger . |
| 5,243,093 | 9/1993 | Kissinger et al. . |
| 5,315,042 | 5/1994 | Cipullo et al. . |
| 5,414,151 | 5/1995 | Pressman et al. . |
| 5,874,644 | 2/1999 | Gammill ................................. 568/724 |

FOREIGN PATENT DOCUMENTS 109033  5/1984  European Pat. Off. .

OTHER PUBLICATIONS

International Search Report for Application No. PCT/US 99/13885 (1999).

*Primary Examiner*—Michael L. Shippen

[57] ABSTRACT

An improved process for producing Bisphenol-A which is essentially free of sodium impurity using rotary vacuum filter pumps which utilize a liquid ring seal to effect drawing a vacuum on a Bisphenol-A/phenol slurry, the improvement is in using phenol as the liquid ring seal medium.

6 Claims, No Drawings

LIQUID VACUUM PUMP SEAL TO REDUCE CONTAMINATION IN BISPHENOL-A

FIELD OF THE INVENTION

This invention relates to a rotary vacuum pump employing a particular pump seal liquor in order to eliminate contamination in the production of dihydric phenols particularly Bisphenol-A which is used in substantial quantities to synthesize polymers particularly aromatic carbonate polymers. The novel feature of this invention is employing liquid phenol as the vacuum pump seal liquor as will be described hereinafter.

BACKGROUND OF THE INVENTION

Bisphenol-A has been an extremely useful chemical for many decades. AS a difunctional monomer, it has been used in the preparation of numerous polymers. For example Bisphenol-A [2,2'-bis(4-hydroxyphenyl)propane] has been utilized in preparing such materials as epoxy resins, polyetherimides, polyarylates and, in particular, polycarbonates. In certain of these polymer systems, particularly the epoxy systems, the purity of the Bisphenol-A (hereinafter referred to as BPA) employed in the polymer reaction need not be that high. Epoxy resins only need BPA of approximately 95% purity. The impurity which is present in the greatest amount in such systems is generally orthopara BPA. However with other polymer systems, particularly polycarbonates, the purity of the BPA must be substantially higher. Purities of BPA of about 99.50% or higher preferably 99.80 or 99.90% or higher are desirable and in many cases necessary for the preparation of BPA polycarbonates. Therefore there has been substantial attention directed to the preparation and purification of BPA.

The art is replete with references directed to the preparation of BPA. Usually this is done by the condensation of phenol with acetone in the presence of a catalyst system. Generally the catalyst is an acidic catalyst. For many years one of the particularly useful catalyst systems in the patent art and employed commercially was hydrochloric acid. Although the economics of the process are initially good with respect to the conversion of the reactants to BPA, the maintenance of the apparatus is costly. The hydrochloric acid is extremely corrosive and ordinary metallic reactors and piping must be changed on a frequent basis. Obviously glass lined reactors or certain alloyed metals can be employed, however, these are quite expensive. In later years there seems to be the tendency to use heterogeneous acidic catalyst system wherein the acidic catalyzation occurs at the catalyst surface and is actually bound to the catalyst. in this manner the "acid" does not flow with the unused reactants and BPA. Such catalyst systems are generally sulfonated polystyrenes which are substantially crosslinked such as the Amberlites and like materials. However, such sulfonated polystrenes, because they contain sulfonic pendent groups may form sulfonic acids. The sulfonic acids, along with hydrochloric acid, if employed as part of or a contaminant in the catalyst system, and any other acids can be very corrosive to the equipment, particularly rotary vacuum pumps. Consequently, aqueous caustic has been used as the liquid vacuum seal in rotary vacuum pumps in order to neutralize the acids in the BPA condensation reaction products generally comprised of BPA, phenol, and water and other materials. The reaction products are sent to a crystallizer system wherein a BPA/phenol crystal slurry is formed. The slurry is sent to a rotary vacuum filter, equipped with vacuum pumps which pull the slurry through a filter drum.

A cake (BPA/phenol adduct) is formed on the drum and the extracted liquid often referred to as the mother liquor is recycled to the reactor in which BPA is formed. The mother liquor may be subjected to dehydration in order to remove water of reaction and other unwanted materials before recycling the mother liquor back to the reactor. Optionally, the BPA adduct may be redissolved in phenol and sent to a second rotary filter (second stage) equipped with vacuum pull for further purification.

After the BPA is prepared, various isolation and purification procedures are known. Many of these appear in the relatively voluminous patent art. Generally phenol is distilled off to a great extent and/or the initial purification by adduct crystallization of the BPA/phenol adduct Distillation of BPA itself can also be employed. The purification of the BPA can then be further accomplished through the addition of various organic solvents such as toluene or methylene chloride so as to remove the BPA from various impurities. Additionally water and various glycols such as ethylene glycol and glycerin have been used alone or together to separate and thus purify the BPA from its impurities.

Therefore, it is an object of this invention to provide a process whereby sodium ions are not introduced into the BPA.

Another object of this invention is to employ liquid phenol as a seal liquor in rotary vacuum pumps.

The foregoing and other objects of this invention will become apparent from the following description and appended claims.

SUMMARY OF THE INVENTION

In accordance with the invention, there is a method of reducing contamination in BPA upon separating an adduct slurry and a mother liquor. In the process of separating the adduct slurry from the mother liquor, rotary vacuum filters may be employed. The rotary vacuum filters are operated under a vacuum wherein the pressure is controlled at a level below atmospheric and operate in a range of 50 mm Hg to about 250 mm Hg absolute. In systems employing rotary vacuum filters, the rotary filters may be mechanical liquid ring pumps to provide the vacuum source. In such systems, aqueous caustic (sodium hydroxide/water) solution has been used to provide the liquid seal for these pumps. The fans or blades of the pump cannot touch the inside of the pump housing since wear would be extremely extensive. The vacuum pump seal liquor is essential to the ability of the pumps to pull a vacuum (reduced pressure) down to the operating level. Sodium hydroxide solution has been used as the liquid seal in such pumps when producing BPA as described heretofore. However, it has been determined that small amounts of acidic and/or basic ionic contamination, such as sodium, are catalytic in causing undesirable reactions to occur in the BPA and/or polymer products produced therewith such as aromatic carbonate polymers.

It has also been determined that the use of aqueous sodium hydroxide solutions as pump seal liquor provides for a direct source of process contamination with sodium.

It has now been discovered that by employing phenol as a liquid ring seal for a rotary pump, undesirable contamination from sodium hydroxide solution is completely eliminated.

DETAILED DESCRIPTION OF THE INVENTION

BPA is generally prepared by the reaction of phenol and acetone in the presence of an acidic catalyst, such as HCl or an ion exchange resin. During the reaction, some unwanted by-products and color are formed which affect yield and quality. Also in the filtration of a BPA/phenol adduct slurry generally comprising a liquor (often referred to as a mother liquor), BPA and phenol, the adduct slurry is deliquored by vacuum filtration which slurry comprises BPA and phenol. The mother liquor is essentially recycled back to the reaction for producing BPA as described heretofore.

In the filtration system, rotary vacuum filters are used to separate the adduct cake from the mother liquor. The process for producing the BPA can be any process and is not critical in the practice of this invention. The critical feature is the use of phenol as the liquid in a liquid ring seal rotary pump. These pumps are employed to provide a vacuum source for removal or separation of the mother liquor from the adduct slurry. AS stated previously, the use of sodium hydroxide as the liquid ring seal in rotary vacuum pumps introduces contamination into the BPA. The use of phenol essentially eliminates undesirable sodium contamination from the BPA. In addition, it has also been surprisingly discovered that the use of phenol results in the elimination of an amount of waste water that would come from the aqueous caustic, which waste water must be recovered for environmental purposes. This also results in significant reduction in process investment and operating costs by eliminating these water sources.

Another advantage is that it is possible to discontinue the use of sulfuric acid which is required to neutralize the aqueous caustic effluents which are contaminated with phenol.

Since phenol is a solid at room temperature, the phenol used as a liquid seal is kept at a temperature above its melting point under process conditions such that it is in a liquid state, preferably at a temperature of at least about 150° C. and more preferably at a temperature of about 150 to about 175° F.

In another embodiment of this invention, a small amount of fresh phenol may be continuously fed to the rotary pumps. The replaced or used phenol may then be treated for removal of contaminants before recycling the replaced phenol back to the reactor for forming BPA. Since phenol does not neutralize the acid contaminants as described heretofore when employing aqueous caustic, the acid contaminants can be removed by continuously feeding fresh phenol to the rotary vacuum pumps. The replaced or used phenol will carry off the acid contaminants.

The following examples are intended to provide exemplification of the invention and are not intended to limit the invention.

EXAMPLE 1

A two stage rotary vacuum pump system is employed to obtain a BPA/phenol cake. After each stage, a BPA/phenol cake is obtained by crystallization and vacuum filtering a BPA/phenol adduct (slurry). After the first stage, the cake is dissolved in phenol and the liquid system is then sent to a second stage or second rotary vacuum pump. In each stage, the rotary vacuum pump has a sodium hydroxide (caustic) liquid vacuum pump seal. Three different flow rates are evaluated and, in each case, the BPA/phenol cake after the second stage is analyzed for sodium (Na) contamination in the BPA/phenol cake. The results obtained are as follows:

TABLE 1

| Flow Rate of Caustic Seal Liquor | Na in BPA/phenol Cake |
|---|---|
| 5 Kg/hr. | 30 ppb |
| 10–11 Kg/hr. | 50–60 ppb |
| 15 Kg/hr. | 90 ppb |

Kg-Kilograms
Ppb-parts per billion

The sodium hydroxide solution employed as a liquid seal is a 6.0 weight % aqueous sodium hydroxide.

EXAMPLE 2

Example 1 is repeated except that in place of the caustic liquid seal ring, liquid phenol is employed herein. The liquid phenol is at a temperature of about 160° F.

It is found that when analyzing for sodium in the BPA/phenol cake no sodium was detected at the parts per billion level.

What is claimed is set forth in the claims appended to the application. Variations in this invention may be made without departing from the scope of the claims appended hereto.

What is claimed:

1. An improved process for preparing bisphenol-A with reduced contaminants which process comprises preparing bisphenol-A by reacting phenol and acetone in the presence of a catalyst crystallizing the residue of the reaction to a bisphenol-A/phenol crystal slurry, and separating bisphenol-A/phenol crystals from the bisphenol-A/phenol slurry by pulling the slurry through a filter equipped with a rotary vacuum pump which utilizes a liquid ring seal in the vacuum pump to provide a vacuum, the improvement comprising the step of using liquid phenol as the liquid ring seal in said vacuum pump and said phenol is at a temperature above its melting temperature under process conditions.

2. The improved process of claim 1 wherein the temperature of the phenol is at least 150° F.

3. The improved process of claim 1 wherein the liquid phenol is used to replace liquid sodium hydroxide solution as the liquid ring seal in rotary pump.

4. The improved process of claim 1 wherein an amount of sodium present in BPA produced in the process is undetectable at the parts per billion level.

5. The improved process of claim 1 wherein the process further comprises the steps of replacing continuously the liquid seal phenol with fresh phenol, removing acid contaminants absorbed by the replaced phenol and recycling the replaced phenol to the reaction step of reacting phenol and acetone to prepare BPA.

6. The improved process of claim 1 wherein the process further consists essentially of the steps of continuously replacing the liquid phenol used as the liquid ring seal with fresh phenol, removing the replaced phenol and recycling the replaced phenol to the reaction step of reacting phenol and acetone to prepare BPA.

* * * * *